United States Patent
Feigen et al.

(10) Patent No.: US 6,387,880 B1
(45) Date of Patent: May 14, 2002

(54) TRANSDERMAL N-[N-[5-[4-(AMINOIMINOMETHLY)PHENYL]-1-OXOPENTYL]-L-α-ASPARTYL]-L-PHENYLALAININE OR ITS ESTERS AND THEIR PHARMACEUTICALLY ACCEPTABLE SALTS

(75) Inventors: Larry P. Feigen, Wauconda; Martin John Griffin, Skokie, both of IL (US)

(73) Assignee: G.D. Searle & Co., Chicago, IL (US)

( * ) Notice: Subject to any disclaimer, the term of this patent is extended or adjusted under 35 U.S.C. 154(b) by 0 days.

(21) Appl. No.: 08/633,734

(22) PCT Filed: Oct. 24, 1994

(86) PCT No.: PCT/US94/11921

§ 371 Date: Apr. 22, 1996

§ 102(e) Date: Apr. 22, 1996

(87) PCT Pub. No.: WO95/13825

PCT Pub. Date: May 26, 1995

(51) Int. Cl.$^7$ .......................... A61K 31/44; A61K 38/00
(52) U.S. Cl. ......................................... 514/18; 514/357
(58) Field of Search ................................... 514/18, 357

(56) References Cited

U.S. PATENT DOCUMENTS

| | | |
|---|---|---|
| 4,517,686 A | 5/1985 | Ruoslahti et al. ............. 3/1 |
| 4,578,079 A | 3/1986 | Ruoslathti et al. ............ 623/11 |
| 4,589,881 A | 5/1986 | Pierschbacher et al. ....... 623/11 |
| 4,614,517 A | 9/1986 | Ruoslahti et al. ............ 623/11 |
| 4,661,111 A | 4/1987 | Ruoslahti et al. ............ 623/11 |
| 4,683,291 A | 7/1987 | Zimmerman et al. ........ 530/324 |
| 4,857,508 A | 8/1989 | Adams et al. ................ 514/18 |
| 4,879,313 A | 11/1989 | Tjoeng et al. ............... 514/616 |
| 5,220,050 A | 6/1993 | Bovy et al. .................. 514/357 |

FOREIGN PATENT DOCUMENTS

| | | | |
|---|---|---|---|
| EP | 0275748 | 7/1988 | ............ C07K/7/06 |
| EP | 0298820 | 1/1989 | ............ C07K/7/06 |
| EP | 0372486 | 6/1990 | ......... C07C/279/14 |
| EP | 0381033 | 8/1990 | ......... C07C/311/19 |
| EP | 384362 | 8/1990 | ............ C07K/5/10 |
| EP | 0410540 | 1/1991 | ............ C07K/7/06 |
| EP | 92/103861.8 | 9/1992 | ............ C07K/5/02 |
| EP | 92/107757.4 | 11/1992 | ............ C07K/5/06 |
| WO | US 92/01531 | 9/1992 | ............ C07K/5/06 |
| WO | 9215607 | * 9/1992 | |
| WO | US 92/10021 | 6/1993 | ......... C07C/257/18 |
| WO | 92/10526 | 6/1993 | ......... C07D/307/32 |
| WO | 93/01185 | 8/1993 | ......... C07C/311/19 |
| WO | US93/04660 | 12/1993 | ............ C07K/5/06 |
| WO | US93/07975 | 3/1994 | ............ C07K/5/06 |

OTHER PUBLICATIONS

Kloczewiak, et al. *Biochem.*, 23, 1767–1774 (1986).
Ruggeri, et al. *Proc. Natl. Acad. Sci.*, 83, 5708–5712 (1986).
Plow, et al. *Proc. Natl. Acad. Sci.*, 82, 8057–8061 (1985).
Ginsberg, et al. *J. Biol. Chem.*, 260, (7), 3931–3936 (1985).
Haverstick, et al. *Blood*, 66, (4), 946–952 (1985).
Ruoslahti and Pierschbacher *Science*, 238, 491–497 (1987).

* cited by examiner

*Primary Examiner*—Kevin E. Weddington
(74) *Attorney, Agent, or Firm*—Fitzpatrick, Cella, Harper & Scinto

(57) ABSTRACT

The present invention is for pharmaceutical compositions and a method of use for the transdermal delivery of N-[N-[5-[4-(aminoiminomethyl)phenyl]-1-oxopentyl]-L-α-aspartyl]-L-phenylalanine or its esters and their pharmaceutically acceptable salts which are useful as platelet aggregation inhibitors.

10 Claims, No Drawings

TRANSDERMAL N-[N-[5-[4-(AMINOIMINOMETHLY)PHENYL]-1-OXOPENTYL]-L-α-ASPARTYL]-L-PHENYLALAININE OR ITS ESTERS AND THEIR PHARMACEUTICALLY ACCEPTABLE SALTS

FIELD OF THE INVENTION

The present invention is for pharmaceutical compositions for transdermal delivery of N-[N-[5-[4-(aminoiminomethyl)phenyl-1-oxopentyl]-L-α-aspartyl]-L-phenylalanine or its esters and their pharmaceutically acceptable salts which are useful as platelet aggregation inhibitors.

BACKGROUND OF THE INVENTION

N-[N-[5-[4-(aminoiminomethyl)phenyl]-1-oxopentyl]-L-α-aspartyl]-L-phenylalanine which is represented by the following formula

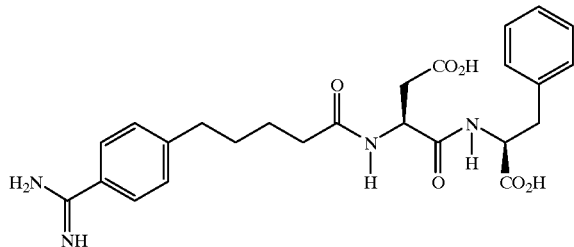

or its esters and their pharmaceutically acceptable salts are known to be useful as platelet aggregation inhibitors. See International Publication W092/15607, published Sep. 17, 1992.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as gpIIb/IIIa; this is an important feature of the platelet function. Inhibitors of this interaction are useful in modulating platelet thrombus formation.

Initially, N-[N-[5-[4-(aminoiminomethyl)phenyl]-1-oxopentyl]-L-α-aspartyl]-L-phenylalanine or its esters and their pharmaceutically acceptable salts were administered orally, parenterally, rectally or by inhalation spray. See International Publication W092/15607, published Sep. 17, 1992.

These prior conventional methods of administering drugs to patients, however, possess certain shortcomings.

The oral route of drug administration, for example, is inadequate for several reasons, even if the drug is administered to the patient at periodic intervals according to a well-defined schedule.

The rate of absorption of drug through the gastrointestinal tract is affected by both the contents in the tract and the passage of time as the drug travels through the small intestine. Therefore, such variables as whether the drug is administered before or after eating, and the type and quantity of food eaten, for example, high or low fat content, or whether the drug is administered before or after bowel movement, affect the rate of absorption of the drug which takes place in the small intestine.

Additionally, the time of passage of drug through the small intestine is affected by the rate of peristaltic contraction, adding further uncertainty.

Also important is the rate of circulation of blood to the small intestine, and the fact that many drugs administered by this route are rendered inactive by gastric acid, digestive enzymes of the gastrointestinal tract, or by liver, where the drug can be metabolized to an inactive product.

These factors make it difficult to achieve a desired time course of concentration of drug in the blood.

The most inevitable result of the oral administration of drugs through the gastrointestinal tract is that the level of drug in circulation surges to a peak level shortly after the time of drug administration, followed by a decline in drug concentration in the blood and body compartments.

The administration of drugs by injection likewise entails certain disadvantages. For example, very strict asepsis must be maintained in order to avoid infection of the blood, the vascular system and the heart. Drug administration by poor intravenous technique may result in perivascular injection, when that was not intended. The typical result of injection of a drug into the blood is a sudden rise in the blood concentration of the drug followed by an uncontrollable decline in drug concentration. Additionally, administration of drugs by injection is inconvenient and painful.

Other dosage forms for systemic administration of drugs, such as rectal suppositories and sublingual lozenges, also produce non-uniform levels of the therapeutic agent in circulation. These dosage forms require great patient cooperation and have low patient acceptability, resulting in decreased patient compliance with a prescribed drug regimen, which is the most common failure of drug therapy.

The present invention is a new form of administration of N-[N-[5-[4-(aminoiminomethyl)phenyl]-1-oxopentyl]-L-α-aspartyl]-L-phenylalanine or its esters and their pharmaceutically acceptable salts into a transdermal pharmaceutical composition to achieve blood levels which are effective in the inhibition of platelet aggregation. Particularly interesting compounds which are representative of this above-described class of compounds are exemplified by N-[N-[5-[4-(aminoiminomethyl)phenyl]-1-oxopentyl]-L-α-aspartyl]-L-phenylalanine, hydrochloride;

N-[N-[5-[4-(aminoiminomethyl)phenyl]-1-oxopentyl]-L-α-aspartyl]-L-phenylalanine, diethyl ester;

N-[N-[5-[4-(aminoiminomethyl)phenyl]-1-oxopentyl]-L-α-aspartyl]-L-phenylalanine, dimethyl ester; and N-[N-[5-[4-(aminoiminomethyl)phenyl]-1-oxopentyl]-L-α-aspartyl]-L-phenylalanine, acetate.

Transdermal delivery of N-[N-[5-[4-(aminoiminomethyl)-phenyl]-1-oxopentyl]-L-α-aspartyl]-L-phenylalanine or its esters and their pharmaceutically acceptable salts offers advantages over the other methods of delivery which were discussed above. An advantage is the ease of application over the intravenous or intramuscular delivery. This convenience of use offers the benefit of a lifestyle uninterrupted by hospital visits, which are needed when administering by other known methods. Administration by IV or intramuscular delivery has certain disadvantages of inadvertent needle sticks. Needle sticks have also been associated with the risk of secondary systemic infections. Transdermal delivery does provide the ability to deliver drugs directly to general circulation. Effective transdermal delivery affords a controlled, constant, zero-order release of active compound. Transdermal delivery is greatly advantageous in that it can be used in pediatric age groups, where IV or IM dosing is very difficult.

Another advantage of transdermal delivery is that the delivery of the active can be rapidly terminated by removing the patch. Other routes of delivery do not possess this most desirable advantage.

Recognizing that the outer layer of the skin, the epidermis, protects the area under the skin from penetration of foreign chemicals, various enhancing agents have been used to deliver drugs transdermally. Substances that help promote drug diffusion through the stratum corneum and epidermis are referred to as skin-penetration enhancers, accelerants, adjuvants and absorption promoters. B. Idson, *Cosmetics & Toiletries*, 95, 59 (1980) states that the factors affecting drug penetration and consequently in most cases, effectiveness, are complex. The vehicle that provides ideal conditions for one drug may prove unsatisfactory for another.

Various penetration enhancers are known to be useful in transdermal drug delivery. U.S. Pat. No. 4,863,970, U.S. Pat. No. 4,722,941, U.S. Pat. No. 4,931,283 and EP 351,897 disclose some representative penetration enhancers used in transdermal compositions and for topical administration.

SUMMARY OF THE INVENTION

The present invention provides a pharmaceutical formulation in the form of a transdermal delivery system comprised of N-[N-[5-[4-(aminoiminomethyl)phenyl]-1-oxopentyl]-L-α-aspartyl]-L-phenylalanine or its esters and their pharmaceutically acceptable salts and a delivery solvent. Effective delivery solvents for the practice of this invention are exemplified by ethanol and n-methyl pyrrolidone.

It is the primary object of this invention to provide a pharmaceutical composition for transdermal delivery of N-[N-[5-[4-(aminoiminomethyl)phenyl]-1-oxopentyl]-L-α-aspartyl]-L-phenylalanine or its esters and their pharmaceutically acceptable salts.

DETAILED DESCRIPTION OF THE INVENTION

This invention encompasses pharmaceutical compositions for transdermal delivery of N-[N-[5-[4-(aminoiminomethyl)phenyl]-1-oxopentyl]-L-α-aspartyl]-L-phenylalanine or its esters and their pharmaceutically acceptable salts. Particularly, this invention encompasses pharmaceutical compositions of N-[N-[5-[4-(aminoiminomethyl)phenyl-1-oxopentyl]-L-α-aspartyl]-L-phenylalanine, hydrochloride; and N-[N-[5-[4-(aminoiminomethyl) phenyl]-1-oxopentyl]-L-α-aspartyl]-L-phenylalanine, diethyl ester for transdermal delivery.

The term "pharmaceutically acceptable salt" refers to a salt prepared by acid-base reactions. Examples of pharmacologically acceptable salts include the hydrochloride, hydrobromide, hydroiodide, sulfate, phosphate, acetate, propionate, lactate, maleate, malate, succinate, and tartrate salts. All of these salts may be prepared by conventional means known by those of ordinary skill in the art. The most preferred salt is the hydrochloride.

The term "esters" refers to a radical having the following formula

—COOR wherein the portion defined by R refers to a linear or branched saturated hydrocarbon group having 1 to 6 carbon atoms. Illustrative of such groups are methyl, ethyl, propyl, isopropyl and butyl.

The term "composition" as used herein means a product which results from the mixing or combining of more than one element or ingredient.

The term "pharmaceutically-acceptable carrier" as used herein means a pharmaceutically acceptable material, composition or vehicle, such as a liquid or solid filler, diluent, excipient, or solvent involved in carrying or transporting a chemical agent from one organ or portion of the body to another organ or portion of the body.

The term "transdermal delivery" as used herein means administration of the pharmaceutical composition topically to the skin wherein the active ingredient, or its pharmaceutically acceptable salts, will be percutaneously delivered in a therapeutically effective amount.

The term "penetration enhancers" as used herein means compounds which enhance the percutaneous absorption of drugs. Selection of an effective penetration enhancer for a particular drug must be experimentally deduced. A penetration enhancer which works for one drug will not necessarily work for every other drug B. Idson, *Cosmetics & Toiletries*, 95, 59 (1980).

The term "delivery solvent" as used herein means a solvent in which the dissolution (dissolving of the active or compound into the solvent) is complete.

In the present invention N-[N-[5-[4-(aminoiminomethyl)-phenyl]-1-oxopentyl]-L-α-aspartyl]-L-phenylalanine or its esters and their pharmaceutically acceptable salts are administered transdermally by topical application of N-[N-[5-[4-(aminoiminomethyl)phenyl]-1-oxopentyl]-L-α-aspartyl]-L-phenylalanine or its esters and their pharmaceutically acceptable salts to the skin. More preferably these compounds can be administered in the form of a gel and covered with a suitable impenatrable membrane. The pharmaceutical compositions of the present invention can administer the N-[N-[5-[4-(aminoiminomethyl)phenyl]-1-oxopentyl]-L-α-aspartyl3-L-phenylalanine or its esters and their pharmaceutically acceptable salts in admixture with a delivery solvent and suitable pharmaceutical diluents, carriers and excipients such as gelling agents, emollients, (i.e., allantoin and preservatives (i.e., parabens). Preferably N-[N-[5-[4-(aminoiminomethyl)-phenyl]-1-oxopentyl]-L-α-aspartyl]-L-phenylalanine or its esters and their pharmaceutically acceptable salts are administered in admixture with a delivery solvent.

Delivery solvents suitable for the delivery of N-[N-[5-[4-(aminoiminomethyl)phenyl]-1-oxopentyl]-L-α-aspartyl]-L-phenylalanine or its esters and their pharmaceutically acceptable salts are ethanol and N-methyl pyrrolidone. A preferred solvent is ethanol. The solvents are present in the range of 75 to 95%.

The practicality of administering a given drug percutaneously on a continuous basis depends upon the concentration of drug in the blood that is required to provide the desired pharmacologic effect, the degree to which the skin is permeable to the drug, and the amount of skin surface area that is available for drug administration.

The skin surface area which is available for drug administration, while theoretically being unlimited, is, for practical reasons, typically confined to a range Of from about 1 square centimeters to about 100 square centimeters. With the available skin surface area fixed within this range, the matter then narrows as to whether sufficient drug will pass through the defined skin surface area to provide the desired therapy. If it will, then it may not be difficult to effectively administer the drug percutaneously. If, however, the inherent permeability of the skin to the drug is so high or so low that too much or too little drug will pass through that area of skin, then the rate of administration of the drug to the skin must be controlled, or the permeability of the skin to the drug must be increased, as the case may be, to take percutaneous administration practical.

In order to inhibit platelets from aggregating, use of a non-toxic but therapeutically effective amount of a N-[N-[5-[4-(aminoiminomethyl)phenyl]-1-oxopentyl]-L-α-aspartyl]-L-phenylalanine or its esters and their pharmaceutically acceptable salts is employed. The dose regimen for inhibiting platelet aggregation is selected in accordance with a variety of factors including the type, age, weight, sex and medical condition of the patient. A physician of ordinary skill can readily determine and prescribe an effective amount of the drug required to prevent or treat the progress of condition.

In order to achieve the desired therapeutic effect N-[N-[5-[4-(aminoiminomethyl)phenyl]-1-oxopentyl]-L-α-aspartyl]-L-phenylalanine or its esters and their pharmaceutically acceptable salts parenterally, a dose of 10–50 mg/day is administered. N-[N-[[5-[4-(aminoiminomethyl)phenyl]-1-oxopentyl-L-α-aspartyl]-L-phenylalanine or its esters and their pharmaceutically acceptable salts administered transdermally achieves similar plasma concentrations as the parenteral route of administration. In the preferred embodiment of the present invention N-[N-[5-[4-(aminoiminomethyl)phenyl]-1-oxopentyl]-L-α-aspartyl]-L-phenylalanine or its esters and their pharmaceutically acceptable salts are administered in an amount of 100–500 mg/patch. In a more preferred embodiment of the present invention N-[N-[5-[4-aminoiminomethyl)phenyl]-1-oxopentyl]-L-α-aspartyl]-L-phenylalanine or its esters and their pharmaceutically acceptable salts are delivered in an amount of 10–50 mg/day.

These doses were selected in order to achieve blood levels equivalent to that achieved with parenteral dosing. The required dose of active ingredient to be administered will vary with, amongst other factors, the severity of the condition being treated, and will depend on whether the treatment is remedial or prophylactic.

In order to administer the dose set out above the concentration of N-[N-[5-[4-aminoiminomethyl)phenyl]-1-oxopentyl]-L-α-aspartyl]-L-phenylalanine or its esters and their pharmaceutically acceptable salts in the composition can be from 1 to 20 w/w. The concentrating of N-[N-[5-[4-(aminoiminomethyl)phenyl]-1-oxopentyl]-L-α-aspartyl]-L-phenylalanine or its esters and their pharmaceutically acceptable salts is however preferably from 5 to 20 w/w.

The pharmaceutical compositions of the invention can be made, for example, by addition of a gel to a solution of the phenylamidine derivative. The solution gels and can be poured into a measuring-dispensing device. The gel can be extruded into sealable gel-tubes or syringes. The gel can be applied to the skin in a measured dose, dependent on the factors discussed above and covered with an impenetrable membrane.

Alternatively, the composition can be incorporated in a transdermal patch for delivery percutaneously. Methodology and design of transdermal patches for drug delivery are well known in the pharmaceutical art.

The following examples describe and illustrate the methods for the preparation of the pharmaceutical compositions of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the transdermal compositions of the present invention.

EXAMPLE 1

Rats (male, VAF CD (SD) (BR) were provided with an Elizabethan Collar (HARVARD APPARATUS CO., # 59-6413). Animals were carefully shaved to avoid skin irritation or nicks and they were housed in a NALGE plastic rat metabolic cage with water and food continuously available.

Rats were anesthetized with $N_2O/O_2$ and FLUETHANE fluorocarbon anesthesia using a metering device (Quantifier VMC Anesthesia Machine, Matrix Media Inc.) The rat's back was carefully shaved using an electric razor the day before the transdermal experiment, and no abrasions in the skin surface were apparent.

Compound was applied to the skin using a Hilltop Chambers® transdermal delivery plastic device, in which the compound was contained in a 3% hydroxypropyl cellulose gel. The device was glued in place using cyanomethacrylate (Superbinder 495, Newark Electronics).

The aqueous formulation was 2% in N-[N-[5-[4-(aminoiminomethyl)phenyl]-1-oxopentyl]-L-α-aspartyl]-L-phenylalanine, monohydrochloride (10 mg N-[N-[5-[4-(aminoiminomethyl)phenyl]-1-oxopentyl]-L-α-aspartyl]-L-phenylalanine, monohydrochloride 0.5 ml gel/2.5 cm² patch). N(N-[5-[4-(aminoiminomethyl)-phenyl]-1-oxopentyl]-L-α-aspartyl]-L-phenylalanine, monohydrochloride was neutralized to pH 7.4 with KOH and buffered with 5 mM HEPES N-[2-hydroxyethyl] piperazine-N'-[2-ethanesulfonic acid]in 90% water, 10% propylene glycol. The N-methyl pyrrolidone formulation was made by dissolving 100 mg [$^3$H] N-[N-[5-[4-(aminoiminomethyl) phenyl]-1-oxopentyl]-L-α-aspartyl]-L-phenylalanine, monohydrochloride [15 microcuries] in 400 microliters N-methyl pyrrolidone. The 0.5 ml solution was made into a gel by adding 15 mg hydroxypropyl cellulose and incubating at ambient temperatures for 16 hours. Thirty microcuries [$^3$H] N-[N-[5-[4-(aminoiminomethyl)phenyl]-1-oxopentyl]-L-α-aspartyl]-L-phenylalanine, monohydrochloride (specific activity: 928 mCurie/mmol) was added as a tracer. The amount of compound in a sample was calculated from the number of counts detected and the specific radioactivity of the compound in the patch.

Preparation of [$^3$H$_4$] N-[N-[5-[4-(aminoiminomethyl) phenyl]-1-oxopentyl]-L-α-aspartyl]-L-phenylalanine, monohydrochloride.

A solution of N-[N-[5-[4-aminoiminomethyl)phenyl]-1-oxo-4-pentynyl]-L-α-aspartyl ]-L-phenylaline (20.0 mg, 0.042 mmoles) in dimethylformamide (DMF) (20 mL) with 20 mg of 5% Pd/C was evacuated and the reactor was charged with 10 Ci of carrier free tritium gas. The reaction was allowed to proceed at room temperature with stirring for 2 h. The catalyst was removed by filtration, the filtrate diluted with MeOH and water and the solvents and labile tritium were removed under reduced pressure. The residual material (2.7 Ci) was dissolved in 27 mL DMF. An aliquot of the solution indicated no volative tritium when diluted with MeOH, evaporated in a stream of nitrogen gas at room temperature and redissolved in MeOH. The HPLRC radiochemical purity in duplicate analyses was 76.1% [$^3$H$_4$]N-[N-[5-[4-(aminoiminomethyl) phenyl)-1-oxopentyl]-L-α-aspartyl]-L-phenylalanine, acetate salt with a recovery of 93.1% in the PFP system. This analysis also showed less than 1% of either [$^3$H$_2$]N-N-[5-[4-(aminoiminomethyl) phenyl]-1-oxo-4Z-pentenyl]-L-α-aspartyl]-L-phenylalanine or N-[N-[5-[4-(aminoiminomethyl)phenyl]-1-oxo-4E-pentenyl]-L-α-aspartyl]-L-phenylalanine. The radiochemical purity in the C-18 system was 56.0±2.66% with a recovery of 9.6.6±6.54%. HPLC Purification and Isolation of [$^3H_2$] N-[N-[-5-[4-(aminoiminomethyl)phenyl]-1-oxopentyl]-L-α-aspartyl]-L-phenylalanine.

An aliquot of the crude solution in DMF (0.80 mL, 80 mCi) was taken to dryness at 1 mm Hg and 30° C. The residue was dissolved in 0.4 mL of pH 7, 0.072M triethylamine phosphate (TEAP) and a single 0.2 mL injection made onto the preparative HPLC system. The [$^3H_4$] N-[N-[-5-[4-(aminoiminomethyl) phenyl)-1-oxopentyl]-L-α-aspartyl]-L-phenylalanine peak fraction (6.50 to 7.25 min, 3 mL) was diluted with 8 mL of water and assayed for 16.9 mCi of tritium. Isolation of [$^3H_4$]N-[N-[-5-[4-(aminoiminomethyl) phenyl]-1-oxopentyl]-L-α-aspartyl]-L-phanylalanine in EtOH/water was done using a 2 g C-18 MEGA BOND ELUT column and provided 15.9 mCi of product. HPLRC analysis of the extract using the C-18 system indicated a radiochemical purity of 99.5%. HPLRC analysis using the PFP system indicated a radiochemical purity of 97.5%, with a 1.27% impurity.

Preparation of [$^3H_2$]N-[N-[-5-[4-(aminoiminomethyl) phenyl]-1-oxopentyl]-L-α-aspartyl]-L-phenylalanine at 928 mCi/mmole.

An aliquot of the DMF solution of crude [$^3H_4$] N-[N-[5-[4-(aminoiminomethyl)phenyl)-1-oxopentyl]-L-α-aspartyl]-L-phenylalanine, acetate salt (3.00 mL, 300 mCi) was taken to dryness at 1 mm Hg vacuum and 30° C. The residue was dissolved in 1.2 mL pH 7, 0.072M TEAP, and six injections of approximately 200 μL were made on the μBondapak C18 column. The ]$^3H_4$] N-[N-[5-[4-(aminoiminomethyl)phenyl)-1-oxopentyl]-L-α-aspartyl]-L-phenylalanine, acetate salt peak fractions from each injection (approximately 6.50 to 7.25 min) were combined (18 mL) and diluted with 50 mL of water. Analysis for tritium indicated 136 mCi. The aqueous solution was processed through a 10 g C-18 MEGA BOND ELUT column to provide 136 mCi in EtOH/water, with a radiochemical purity of 99.2% [$^3H_4$] N-[N-[5-[4-(aminoiminomethyl)phenyl]-1-oxopentyl]-L-α-aspartyl]-L-phenylalanine on the C-18 system.

The volume of the EtOH/water solution of [$^3H_4$] N-[N-[5-[4-(aminoiminomethyl)phenyl]-1-oxopentyl]-L-α-aspartyl]-L-phenylalanine was reduced on a rotary evaporator at room temperature to 8.2 mL. Unlabelled N-[N-[5-[4-[(aminoiminomethyl)phenyl]-1-oxopentyl]-L-α-aspartyl]-L-phenylalanine, hydrochloride (72.8 mg, 0.140 mmoles) was dissolved in 50 mL of pH 7.0, 0.02 M $NaH_2PO_4$ by adjusting the pH to 9.5 with 1.0 N NaOH, then adding dilute HCl to bring the pH to 7.0. This aqueous solution of [$^3H_4$] N-[N-[5-[4-(aminoiminomethyl)phenyl]-1-oxopentyl]-L-α-aspartyl]-L-phenylalanine was added to the 8.2 mL solution of [$^3H_4$] N-[N-[5-[4-(aminoiminomethyl)phenyl]-1-oxopentyl]-L-α-aspartyl]-L-phenylalanine, along with a 9.8 mL rinse of pH 7, 0.02 M $NaH_2PO_4$ to bring the volume to 68 mL (11.5% ethanol). Preparation of [$^3H_4$] N-[N-[5-[4-(aminoiminomethyl) phenyl]-1-oxopentyl]-L-α-aspartyl]-L-phenylalanine at 1.06 Ci/mmole.

After storage of crude [$^3H_4$] N-[N-[5-[4-(aminoiminomethyl)phenyl]-1-oxopentyl]-L-α-aspartyl]-L-phenylalanine in DMF at −20° for 9 months, the solvents were removed at 1 mm Hg and 40° C. The residue (2.12 Ci) was dissolved in 10.0 mL of 0.072 M TEAP (pH 7.0) and injected onto the Delta Pak C-18 column (50×300 mm). The [$^3H_4$] N-[N-[5-[4-(aminoiminomethyl)phenyl]-1-oxopentyl)-L-α-aspartyl]-L-phenylalanine peak fraction was collected and processed through a 10 g C-18 MEGA BOND ELUT column. The extract (297 mCi) was 80.3% [$^3H_4$] N-[N-[5-[4-(aminoiminomethyl)phenyl]-1-oxopentyl]-L-α-aspartyl]-L-phenylalanine. The purification sequence was repeated, and the product (200 mCi) was 93.9% [$^3H_4$] N-[N-[5-[4-(aminoiminomethyl)phenyl]-1-oxopentyl]-L-α-aspartyl]-L-phenylalanine. The preparative mobile phase was changed to 0.072 M TEAP (pH 4.5)/MeOH/$CH_3CN$ (85/5/10) and a flow of 100 mL/min to better resolve the non-polar impurities. The [$^3H_4$] N-[N-[5-[4-(aminoiminomethyl)phenyl]-1-oxopentyl]-L-α-aspartyl]-L-phenylalanine was re-injected, the peak fraction collected and processed through a 10 g MEGA BOND ELUT colum to provide a solution of 123 mCi of [$^3H_4$] N-[N-[5-[4-(aminoiminomethyl)phenyl]-1-oxopentyl]-L-α-aspartyl]-L-phenylalanine. The radiochemical purity of this product was 99.4±0.11%, with a recovery of 107±1.1%.

Use of [$^3H_4$] N-[N-[5-[4-(aminoiminomethyl)phenyl]-1-oxopentyl]-L-α-aspartyl]-L-phenylalanine or its diethyl ester in the transdermal shaved rat model.

Urine and feces were collected daily after patch application as indicated in the Table I. Counts were combined to achieve the total amount delivered. Urine was counted directly by scintillography (Hionic Fluid, Packard Co., Mark Ill.), while feces, were processed by mechanical mixing in saline followed by oxidization of a dried aliquot to tritiated water in an oxidizer (Oxidizer Machine, Packard).

Table I shows the percent of radiation appearing in the feces and urine. A 2.5 $cm^2$ patch delivered an average of 48 mg of N-[N-[5-[4-(aminoiminomethyl) phenyl]-1-oxopentyl]-L-α-aspartyl]-L-phenylalanine, monohydrochloride into the urine. A 2.5 $cm^2$ patch also delivered an average of 4.6±1.9 mg of N-[N-[5-[4-(aminoiminomethyl) phenyl]-1-oxopentyl)-L-α-aspartyl]-L-phenylalanine diethyl ester.

TABLE I

| Rat # | Mg transported in Feces | | | Mg transported in Urine | | | Total |
|---|---|---|---|---|---|---|---|
| | 24 Hrs | 48 Hrs | 72 Hrs | 24 Hrs | 48 Hrs | 72 Hrs | |
| Transdermal $^3H$ N—[N[5-{4-(aminoiminomethyl)phenyl]-1-oxopentyl]-L-α-aspartyl]-L-phenylalanine, monohydrochloride in N-Methyl Pyrrolidone, Saline, Ethanol and Methanol. | | | | | | | |
| N-methyl Pyrrolidone | | | | | | | |
| 1 | 0.12 | 3.01 | 1.15 | 2.58 | 0.92 | 0.23 | 8.01 |
| 2 | 0.06 | 0.8 | 0.45 | 1.05 | 0.37 | 0.24 | 2.97 |
| 3 | 0.13 | 2.72 | 2.34 | 5.22 | 1.10 | 0.35 | 11.86 |
| 4 | 0.49 | 0.96 | 0.66 | 1.94 | 0.45 | 0.19 | 4.69 |
| | | | | | | Mean = | 6.88 |
| | | | | | | SEM = | 2.27 |
| Saline | | | | | | | |
| 1 | 0.000951 | 0.23 | 0.22 | 0.158 | 0.113 | 0.095 | .66 |
| 2 | 0.000682 | 0.47 | 0.06 | 0.111 | 0.066 | 0.076 | .92 |
| 3 | 0.01399 | 0.57 | 0.2 | 0.12 | 0.135 | 0.064 | 1.23 |
| 4 | 0.04615 | 2.47 | 0.33 | 0.097 | 0.087 | 0.057 | 2.84 |
| 5 | | 3.33 | 0.08 | 0.067 | 0.203 | 0.063 | 4.00 |
| 6 | 0.00582 | 1.23 | 0.34 | 0.112 | 0.142 | 0.071 | 2.00 |
| 7 | 0.00334 | 1.6 | 0.44 | 0.327 | 0.226 | 0.096 | 2.25 |
| | | | | | | Mean = | 1.99 |
| | | | | | | SEM = | 0.72 |
| Ethanol | | | | | | | |
| 1 | 0.00 | 4.27 | 4.49 | 0.15 | 0.46 | 0.19 | 9.56 |
| 2 | 0.00 | 4.16 | 1.36 | 0.16 | 0.25 | 0.11 | 6.04 |
| 3 | 0.20 | 2.57 | 0.64 | 0.19 | 0.22 | 0.17 | 3.99 |
| 4 | 0.03 | 0.10 | 0.23 | 0.18 | 0.33 | 0.07 | 0.94 |
| | | | | | | Mean = | 5.13 |
| | | | | | | SD = | 3.13 |
| Methanol | | | | | | | |
| 1 | 0.70 | 2.23 | 0.67 | 1.14 | 0.00 | 0.18 | 4.92 |
| 2 | 0.42 | 11.86 | 6.63 | 3.60 | 0.44 | 1.37 | 24.93 |
| 3 | 0.67 | 3.33 | 0.41 | 8.18 | 1.86 | 0.27 | 14.05 |

TABLE I-continued

| Rat # | Mg transported in Feces | | | Mg transported in Urine | | | Total |
|---|---|---|---|---|---|---|---|
| | 24 Hrs | 48 Hrs | 72 Hrs | 24 Hrs | 48 Hrs | 72 Hrs | |
| 4 | 0.20 | 0.37 | 0.00 | 1.67 | 1.13 | 0.18 | 3.55 |
| | | | | | | Mean = | 11.71 |
| | | | | | | SD = | 9.6 |
| Transdermal N—[N-[5-[4-(aminoiminomethyl)phenyl]- 1-oxopentyl]-L-α-aspartyl]-L-phenylalanine, diethyl ester in Ethanol and Saline. | | | | | | | |
| Ethanol | | | | | | | |
| 1 | 0.05 | 3.16 | 1.51 | 0.02 | 0.27 | 0.42 | 5.43 |
| 2 | 0.01 | 2.44 | 2.33 | 0.01 | 0.12 | 0.19 | 5.10 |
| 3 | 0.04 | 4.09 | 1.67 | 0.00 | 0.16 | 0.11 | 6.07 |
| 4 | 0.01 | 1.20 | 0.43 | 0.00 | 0.13 | 0.11 | 1.88 |
| | | | | | | Mean = | 4.62 |
| | | | | | | SD = | 1.87 |
| Saline | | | | | | | |
| 1 | 0.48 | 4.59 | 0.84 | 0.19 | 0.20 | 0.09 | 6.39 |
| 2 | 0.67 | 3.88 | 1.17 | 0.17 | 0.16 | 0.11 | 6.16 |
| 3 | 0.02 | 0.61 | 0.49 | 0.00 | 0.15 | 0.05 | 1.32 |
| 4 | 0.02 | 1.21 | 0.67 | 0.00 | 0.13 | 0.10 | 2.09 |
| | | | | | | Mean = | 3.99 |
| | | | | | | SD = | 2.66 |

What we claim is:

1. A pharmaceutical composition or transdermal delivery of compounds having formula:

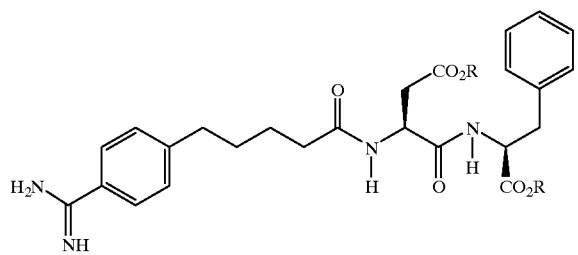

wherein R can be independently hydrogen or alkyl having 1 to 6 carbon atoms or the pharmaceutically acceptable salt comprising:
a therapeutically effective amount of a compound having the formula

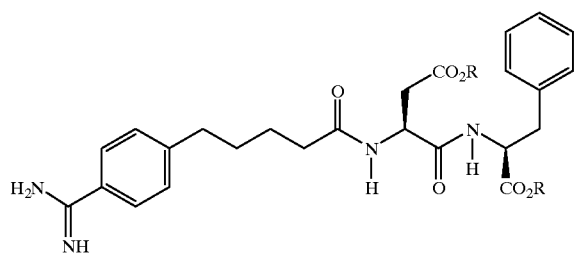

wherein R can be independently hydrogen or alkyl having 1 to 6 carbon atoms or the pharmaceutically acceptable salt; and
a delivery solvent selected from the group consisting of methanol, ethanol, saline and n-methyl pyrrolidone for delivering a therapeutically effective amount of a compound having the formula

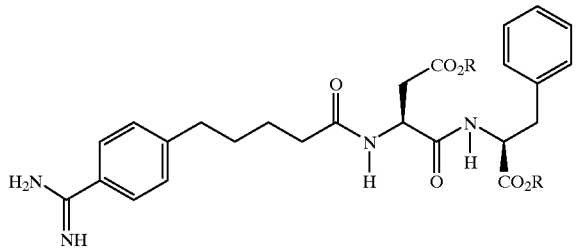

wherein R can be independently hydrogen or alkyl having 1 to 6 carbon atoms or the pharmaceutically acceptable salt through the skin.

2. A composition according to claim 1 wherein the compound is N-[N-[5-[4-(aminoiminomethyl)phenyl]-1-oxopentyl]-L-α-aspartyl]-L-phenylalanine, acetate salt.

3. A composition according to claim 1 wherein the compound is N-[N-[5-[4-(aminoiminomethyl)phenyl]-1-oxopentyl]1-L-α-aspartyl]-L-phenylalanine, diethyl ester.

4. A composition according to claim 1 wherein the compound is N-[N-[5-[4-(aminoiminomethyl)phenyl-1-oxopentyl]-L-α-aspartyl]-L-phenylalanine, dimethyl ester.

5. A composition according to claim 1 wherein the delivery solvent is ethanol.

6. A composition according to claim 1 wherein delivery solvent is n-methyl pyrrolidone.

7. A method of use of a compound having the formula

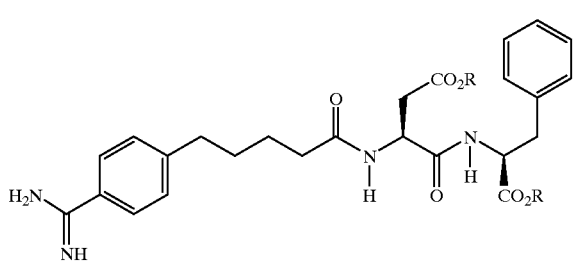

wherein R can be independently hydrogen or alkyl having 1 to 6 carbon atoms or the pharmaceutically acceptable salt, and a delivery solvent selected from the group consisting of methanol, ethanol, saline and n-methyl pyrrolidone for preparing a pharmaceutical composition for the transdermal delivery of a compound having the formula

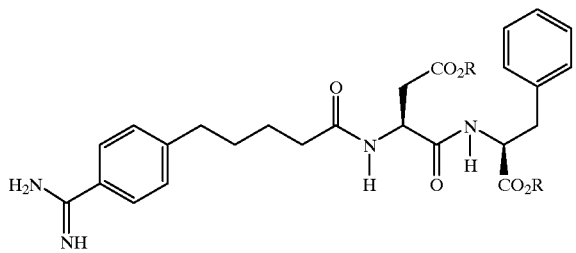

wherein R can be independently hydrogen or alkyl having 1 to 6 carbon atoms or the pharmaceutically acceptable salt; through the skin.

8. A method of use according to claim 7 wherein the compound is [N-[N-[5-[4-(aminoiminomethyl)phenyl-1-oxopentyl]-L-α-aspartyl]-L-phenylalanine] N-[N-[5-[4-(aminoiminomethyl)phenyl]-1-oxopentyl]-L-α-aspartyl]-L-phenylalanine, acetate salt.

9. A method of use according to claim 7 wherein the compound is [N-[N-[5-[4-(aminoiminomethyl)phenyl-1-oxopentyl]-L-α-aspartyl]-L-phenylalanine] N-[N-[5-[4-(aminoiminomethyl)phenyl]-1-oxopentyl]-L-α-aspartyl]-L-phenylalanine, diethyl ester.

10. A method of use according to claim 7 wherein the compound is N-[N-[5-[4-(aminoiminomethyl)phenyl]-1-oxopentyl]-L-α-aspartyl]-L-phenylalanine, dimethyl ester.

* * * * *

UNITED STATES PATENT AND TRADEMARK OFFICE
CERTIFICATE OF CORRECTION

PATENT NO.    : 6,387,880 B1
DATED         : May 14, 2002
INVENTOR(S)   : Larry P. Feigen et al.

It is certified that error appears in the above-identified patent and that said Letters Patent is hereby corrected as shown below:

<u>Title page, Item [54] and Column 1, lines 2 and 4,</u>
"(AMINOIMINOMETHLY)" should read -- (AMINOIMINOMETHYL) --;
"PHENYLALAININE" should read -- PHENYLALANINE --.

<u>Column 1,</u>
Line 10, "phenyl-1-" should read -- phenyl]-1- --.

<u>Column 4,</u>
Line 29, "impenatrable" should read -- impenetrable --;
Line 32, "aspartyl3-L-" should read -- aspartyl]-L- --;
Line 55, "Of" should read -- of --;
Line 56, "centimeters" (first occurrence) should read -- centimeter --;
Line 66, "take" should read -- make --.

<u>Column 6,</u>
Line 25, "N(–" should read -- N-[– --;
Line 47, "-L-phenylaline" should read -- -L-phenylalanine --;
Line 56, "volative" should read -- volatile --.

<u>Column 7,</u>
Line 8, "phenyl)-1-" should read -- phenyl]-1- --;
Line 13, "L-phanylalanine" should read -- L-phenylalanine --;
Line 23, "phenyl)-1-" should read -- phenyl]-1- --;
Line 28, "]$^3$H$_4$]" should read -- [3H$_4$] --;
Line 29, "phenyl)-1-" should read -- phenyl]-1- --.

<u>Column 8,</u>
Line 9, "colum" should read -- column --;
Line 38, "N-[–5-{4-" should read -- N-[–5[4- --.

<u>Column 9,</u>
Line 27, "or" should read -- for --;
Line 28, "formula" should read -- the formula: --.

UNITED STATES PATENT AND TRADEMARK OFFICE
CERTIFICATE OF CORRECTION

PATENT NO.    : 6,387,880 B1
DATED         : May 14, 2002
INVENTOR(S)   : Larry P. Feigen et al.

It is certified that error appears in the above-identified patent and that said Letters Patent is hereby corrected as shown below:

Column 10,
Line 20, "oxopentyl]1-L-" should read -- oxopentyl]-L- --;
Line 22, "phenyl-1-" should read -- phenyl]- --;
Line 64, "[N-[N-[5-[4-(aminoiminomethyl)phenyl-1-oxopentyl]-L-α-aspartyl]-L-phenylalanine]" should be deleted.

Signed and Sealed this

First Day of April, 2003

JAMES E. ROGAN
*Director of the United States Patent and Trademark Office*